United States Patent [19]

Bauer et al.

[11] Patent Number: 5,214,226

[45] Date of Patent: May 25, 1993

[54] METHOD AND APPARATUS FOR THE HOMOGENEOUS CONVERSION OF METHANE

[75] Inventors: Simon H. Bauer; Huy-Zu Cheng, both of Ithaca, N.Y.

[73] Assignee: Cornell Research Foundation, Inc., Ithaca, N.Y.

[21] Appl. No.: 851,406

[22] Filed: Mar. 13, 1992

[51] Int. Cl.$^5$ .............................................. C07C 5/327
[52] U.S. Cl. ................... 585/658; 585/621; 585/500; 585/700; 585/943
[58] Field of Search ................. 585/700, 709, 64, 500, 585/658

[56] References Cited

U.S. PATENT DOCUMENTS

| | | | |
|---|---|---|---|
| 3,980,728 | 9/1976 | Khcheyan et al. | 585/943 |
| 4,197,413 | 4/1980 | Kaeding et al. | 585/468 |
| 4,199,533 | 4/1980 | Benson | 585/657 |
| 4,704,496 | 11/1987 | Paparizos et al. | 585/943 |
| 4,727,205 | 2/1988 | Velenyi et al. | 585/407 |
| 4,727,207 | 2/1988 | Paparizos et al. | 585/415 |
| 4,814,538 | 3/1989 | DeVries et al. | 585/500 |
| 5,081,324 | 1/1992 | Michaels et al. | 585/500 |
| 5,095,161 | 3/1992 | Abrevaya et al. | 585/700 |
| 5,113,032 | 5/1992 | Cameron et al. | 585/700 |

*Primary Examiner*—Anthony McFarlane
*Attorney, Agent, or Firm*—Salzman & Levy

[57] ABSTRACT

The present invention teaches an apparatus and method for commercial conversion of methane in the absence of a catalyst to higher hydrocarbons that are generally in short supply, e.g., butane, ethylene, propene, etc. The production of these higher molecular weight hydrocarbons aids in justifying the cost of the conversion process. The inventive conversion technique utilizes small amounts, generally 1% or less, of a low-cost initiator, plus air, which allows for the commercial viability of the process.

17 Claims, 4 Drawing Sheets

METHOD AND APPARATUS FOR THE HOMOGENEOUS CONVERSION OF METHANE

FIELD OF THE INVENTION

The present invention relates to a method and apparatus for converting methane in the gas phase to other useful products, and, particularly, to a non-catalytic, free radical, methane conversion process wherein the methane can be converted at a practical cost to useful products that are generally in short supply.

BACKGROUND OF THE INVENTION

At present, large quantities of methane are expelled from oil wells and natural gas reserves. Most of these wells are located in remote areas, too distant from cities or chemical processing plants to make transport of the methane practical by pipeline. As a result, most of the well operations treat the methane an expendable byproduct, which is either burned or vented directly into the atmosphere. This is very undesirable, since the burning or venting of the methane into the atmosphere leads to atmospheric pollution and increases the "greenhouse effect" on the planet. In addition, the value of the methane as a resource is wasted.

In some instances, methane is converted to a liquid that can be transported via truck or pipeline. The technique which has been practiced for decades utilizes the Fischer/Tropsch process. The methane is converted to "water gas", i.e., CO and $H_2$, and then catalytically transformed into a mixture of hydrocarbons suitable for use in internal combustion engines. This process, however, is not only considered environmentally undesirable, but it cannot be justified when compared with the cost of processing available crude oil.

Many other methane conversion processes have been proposed, but their lack of practicality, for one reason or another, has thwarted commercialization.

For example, a current benchmark process suggests a three-step technique: (a) steam reformation (b) methanol synthesis, and (c) MTG; i.e.,

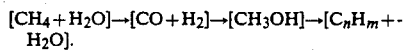

In the most favored approach, the oxidative coupling of methane is utilized, mediated by suitable metal catalysts:

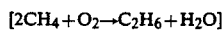

These processes, however, require continuous and careful balancing between homogeneous and heterogeneous reactions. The catalysts have to be periodically regenerated or replaced and are economically unfavorable. Conversion levels are too low. Current wisdom has it that this type of process cannot be optimized beyond its present limits.

Another suggested process, which has been tested only in the laboratory, calls for the direct partial oxidation of methane to methanol. This process is not attractive because it requires precise timing and temperature control, as well as a rapid quench step, all of which make commercialization impractical.

In U.S. Pat. No. 4,199,533 issued to Benson, a process for converting methane to higher molecular weight hydrocarbons by using expensive chlorine gas is described. The chlorine gas is thereby converted to inexpensive hydrochloric acid. Also, the use of chlorine as the catalyst presents serious safety problems.

Processes described in U.S. Pat. No. 4,704,496; 4,727,205; and 4,727,207 utilize the feature of free-radical initiators to facilitate methane conversion under homogeneous (thermal) conditions. While the patented processes suggest operative limits that start at 800° C., and extend to 50 atmospheres of pressure, the experimental data presented in these disclosures do not justify these extended limits. The operative temperature is believed to be viable only above 1,000° C. The use of narrow-bore reaction tubes suggests that the conversions incorporate a substantial portion of surface reactions; therefore, this mitigates against the possibility of upscaling to commercially practicable reactor size. All of the above limitations suggest conversion processes that are not commercially viable.

The prior art also suggests a process of methane conversion utilizing various free radical initiators of questionable efficiency. $N_2O$ as an initiator does generate copious levels of atoms that induce C-H fission and the subsequent chain propagation necessary for the production of higher molecular weight hydrocarbons. The difficult with this prior art technique lies in the high cost of the $N_2O$ initiator, which is consumed in the reaction in large quantities.

The present invention teaches an apparatus and method for commercial conversion of methane to higher hydrocarbons that are generally in short supply, e.g., ethylene, propene, and butane. The production of these higher molecular weight hydrocarbons and their commercial value aid in justifying the cost of the conversion process. The inventive conversion technique utilizes small amounts (generally at or less than 1%) of a low-cost initiator; this allows for the commercial viability of the process.

The current invention modeled test at low temperatures in the general range of 800° to 900° C. The conversion is viable over a wide range of methane pressures, generally at pressures at or below 20 atmospheres. The free-radical generator present at low concentrations is augmented by a comparably low level of oxygen. The process is not subject to a runaway oxidation of methane; thus, it achieves conversion without precise control of residence time in the reactor. Residence time in the reactor can range widely between 10 to 1,000 seconds. The reaction is carried out in a large-bore, thermal-flow reactor, which negates the possibility of unwanted surface reactions but enhances the throughput.

Model computations show that the presence of low levels of higher hydrocarbons, such as ethane, propane, n-butane and iso-butane, naturally comixed with methane effluents from gas and oil wells, enhance the conversion efficiency of methane as practiced in this invention. Furthermore, the presence of low levels of hydrogen sulfide, if less than 1%, does not reduce conversion when oxygen is added at a slightly higher level than 1%.

SUMMARY OF THE INVENTION

In accordance with the present invention, there are provided a non-catalytic, methane conversion process and apparatus that are commercially viable. The technique utilizes low levels of a low-cost, highly abundant, free radical initiator augmented by comparable concentration of oxygen. The initiator, plus the added oxygen, generates copious levels of free H, O or OH radicals under homogeneous conditions and at much lower temperatures than are generally required for significant C—H bond fission. The initiator with oxygen converts the methane in a heated vessel to higher molecular weight hydrocarbons, such as ethylene, propene and/or butane. The net conversion to ethylene, propene or butane is economically viable, when considering the low cost and the small amounts required of the initiator materials.

The initiator of the conversion process comprises one or more highly alkylated butanes or pentanes and/or mixtures thereof. Some preferred initiators for this purpose are 4,4-dimethyl pentene-1; 2,2,3,3-tetramethyl butane; and 2,2,4-trimethyl pentane (iso-octane). These materials are usually natural products of petroleum refining. Iso-octane, in particular, is abundantly available and of low cost.

The process of the invention is generally described by the following sequence of chemical reactions, using a 2,2,3,3-tetramethyl butane as a model initiator:

Radical Initiation: (a)

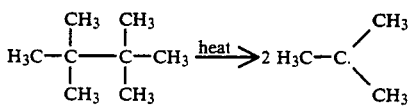

Radical Conversion: (b)

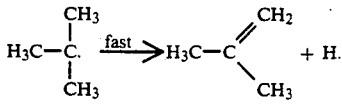

Chain Branching: (c)

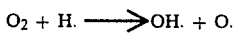

Chain Propagation: (d)

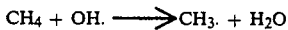

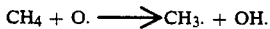

Production of Ethylene: (e)

and numerous other steps

Other hydrocarbons (butane, in particular) are generated in substantial amounts, as illustrated below.

The apparatus of the invention that will carry out the above reactions can comprise one of several types of reactors that will allow for the exposure of the mixture of gases to elevated temperatures under conditions that will not produce substantial wall or surface effects. Appropriate reactors for this process include heated, simple, wide-bore flow tubes or a laser-powered homogeneous pyrolysis reactor. The reactor is fed air, the desired initiator(s) at approximately 1% levels, and a primary methane feedstock. The methane feed gas and admixed air are preheated. The initiator is then injected into the stream, and the mixture is fed into the main reactor, where it is maintained at the desired temperature for a pre-selected residence time. The outflow is cooled and fed to a separation column. There the permanent gases are stripped, and the higher molecular weight hydrocarbons (such as butane, ethylene and propene) are collected. The carbon monoxide and hydrogen from the low boiling distillate are used as fuel for heating the reactor. The unconverted methane is mixed with the direct methane feed and recycled through the conversion process.

BRIEF DESCRIPTION OF THE DRAWINGS

A complete understanding of the present invention may be obtained by reference to the accompanying drawings, when considered in conjunction with the detailed description thereof and in which.

DESCRIPTION OF THE PREFERRED EMBODIMENT

Generally speaking, the invention features a method and apparatus for the conversion of methane, in the absence of a catalyst, into higher molecular weight hydrocarbons, utilizing a free radical reaction. Free radicals are generated thermally by admixed low concentrations of a low-cost initiator. These free radicals react with admixed oxygen and attack methane to produce ethylene, propene and other higher molecular weight hydrocarbons. The relative high cost of the products of these reactions, when compared with the low cost and small amounts of the initiator materials, makes the process one that is profitable.

Figure 1:
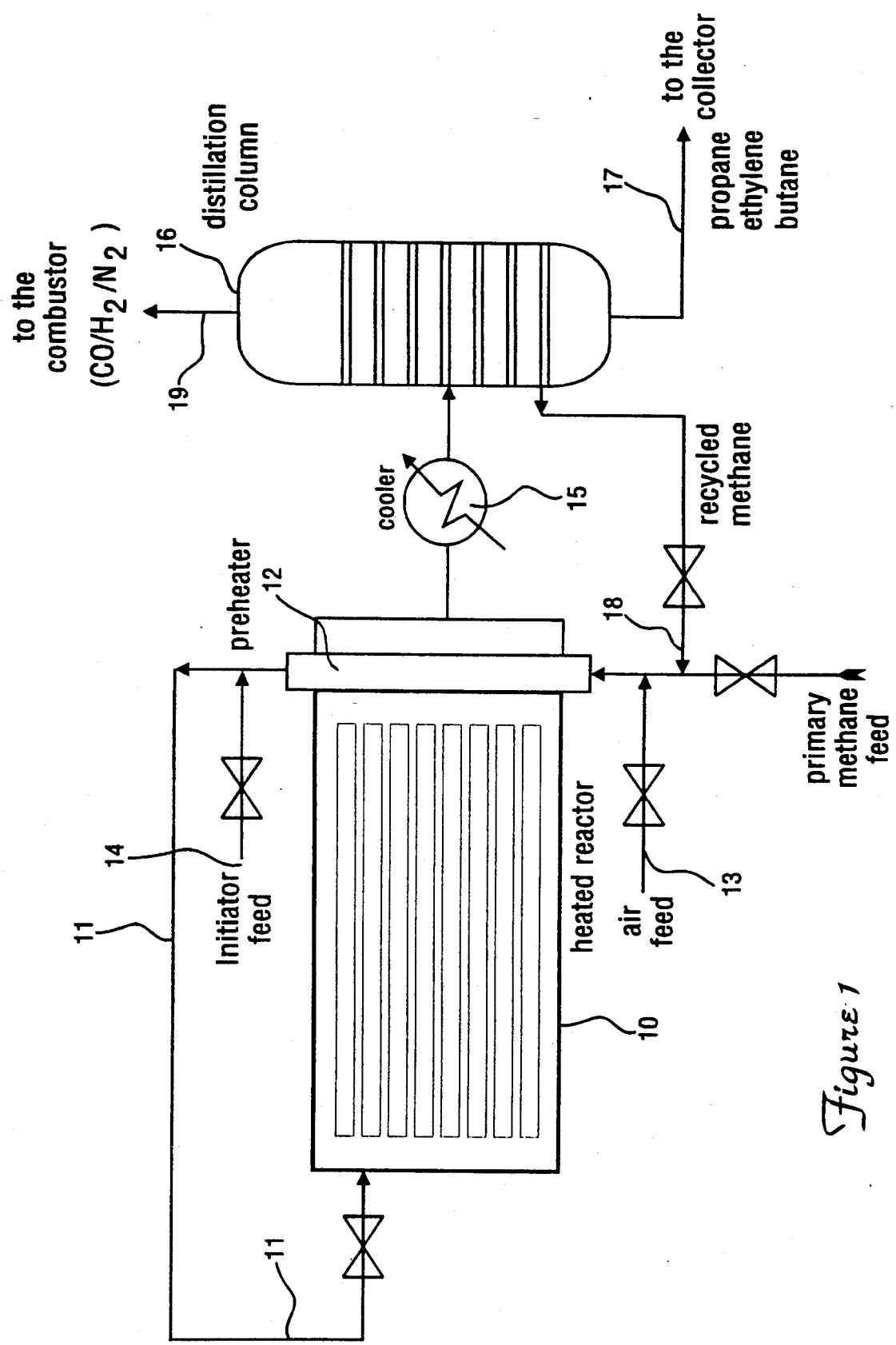
FIG. 1 is a schematic diagram of the apparatus of the invention utilized in the conversion of methane to higher molecular weight hydrocarbons with the use of low-level amounts of an alkane initiator and oxygen.

Now referring to FIG. 1, a schematic diagram of the apparatus for carrying out the process of this invention is shown. The apparatus comprises a heated, flow-through reactor 10, usually operating in the general temperature range of 1,000° to 1,100° K., or, about 800° to 900° C. The reactor 10 can be a parallel set of simple, wide-bore flow tubes. A primary methane feedstock is introduced into the reactor 10 along feed line 11. The methane is preheated in a preheated 12 disposed along line 11. Air and an initiator are also introduced into the reactor 10 along with the methane, along respective lines 13 and 14. The initiator materials can be highly alkylated butanes or pentanes and/or mixtures thereof. Some preferred initiators for this purpose are 4,4-dimethyl pentene-1; 2,2,3,3-tetramethyl butane; and 2,2,4-trimethyl pentane (iso-octane). In the reactor 10, the mixture of methane, air and the initiator react to produce a mixture of products, according to the general reaction scheme set forth below (using 2,2,3,3-tetramethyl butane as a model initiator):

Radical Initiation: (a)

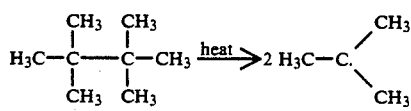

Radical Conversion: (b)

-continued

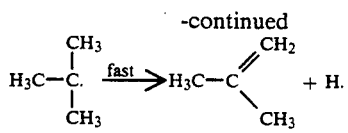

Chain Branching: (c)

Chain Propagation: (d)

Production of Ethylene: (e)

and numerous other steps

Other hydrocarbons (butane, in particular) are generated in substantial amounts.

The reaction products pass through a cooler 15 and into a distillation column 16, where the products are separated and subsequently collected. The propene, ethylene and butane are pumped to a collection tank (not shown) along line 17. Some methane that has not reacted is recycled and fed back to line 11, via line 18. By-products of the reaction, such as carbon monoxide, hydrogen, water and nitrogen leave distillation column 16 via line 19, and can be utilized to fuel the heaters and to maintain the desired temperature of the reactor.

The methane pressures in the reactor may be as high as 20 atmospheres. The reaction time in reactor 10 can be between 10 and 1,000 seconds, depending upon the desired products and desired yields. The optimal combination of reactants is that which, at the end of exposure to the operating temperature, generates the highest levels of olefines and paraffins in proportion to the methane converted, and concurrently the lowest fraction converted to carbon monoxide, considered a by-product. These figures of merit are measured, respectively, by the ratios [b+c] and [a] of TABLE 1.

Representative values of an extended set of calculations are summarized in Table I. The following are figures of merit.

TABLE I

Product distributions for initial methane at 20 atm, 1100° K. (827° C.). INITIATOR - 2,2,3,3 tetramethyl butane (tmb).

| [O2]$_i$ | 0.500 atm | 0.500 atm | 0.200 atm |
|---|---|---|---|
| [Init]$_i$ | 0.112 atm | 0.224 atm | 0.224 atm |
| time(s) | $\kappa = [CH_4]_t/[CH_4]_i$ | | |
| 1.0E−02 | 0.297E−01 | 0.433E−01 | 0.338E−01 |
| 1.0E−01 | 0.852E−01 | 0.895E−01 | 0.679E−01 |
| 1.0E+00 | 0.159E+00 | 0.159E+00 | 0.144E+00 |
| 1.0E+01 | 0.439E+00 | 0.428E+00 | 0.422E+00 |
| 1.0E+02 | 0.872E+00 | 0.871E+00 | 0.871E+00 |
| 1.0E+03 | 0.973E+00 | 0.973E+00 | 0.973E+00 |
| time(s) | $\Delta = [CO]_t/\Delta[CH_4]_t$ | | |
| 1.0E−02 | 0.315E+00 | 0.342E+00 | 0.190E+00 |
| 1.0E−01 | 0.218E+00 | 0.228E+00 | 0.118E+00 |
| 1.0E+00 | 0.120E+00 | 0.129E+00 | 0.564E−01 |

TABLE I-continued

Product distributions for initial methane at 20 atm, 1100° K. (827° C.). INITIATOR - 2,2,3,3 tetramethyl butane (tmb).

| [O2]$_i$ | 0.500 atm | 0.500 atm | 0.200 atm |
|---|---|---|---|
| [Init]$_i$ | 0.112 atm | 0.224 atm | 0.224 atm |
| 1.0E+01 | 0.436E−01 | 0.479E−01 | 0.193E−01 |
| 1.0E+02 | 0.219E−01 | 0.236E−01 | 0.933E−02 |
| 1.0E+03 | 0.197E−01 | 0.212E−01 | 0.837E−02 |
| time(s) | $a = ([CO]_t + [H_2]_t)/\Delta[CH_4]_t$ | | |
| 1.0E−02 | 1.232E+00 | 1.301E+00 | 1.139E+00 |
| 1.0E−01 | 1.052E+00 | 1.108E+00 | 1.029E+00 |
| 1.0E+00 | 0.929E+00 | 0.958E+00 | 0.918E+00 |
| 1.0E+01 | 0.694E+00 | 0.693E+00 | 0.668E+00 |
| 1.0E+02 | 0.749E+00 | 0.747E+00 | 0.735E+00 |
| 1.0E+03 | 0.757E+00 | 0.755E+00 | 0.745E+00 |
| time(s) | $b = ([C_2H_4]_t + [C_3H_6]t)/\Delta[CH_4]_t$ | | |
| 1.0E−02 | 0.465E+00 | 0.588E+00 | 0.730E+00 |
| 1.0E−01 | 0.354E+00 | 0.479E+00 | 0.572E+00 |
| 1.0E+00 | 0.293E+00 | 0.364E+00 | 0.406E+00 |
| 1.0E+01 | 0.849E−01 | 0.972E−01 | 0.102E+00 |
| 1.0E+02 | 0.849E−03 | 0.875E−03 | 0.881E−03 |
| 1.0E+03 | 0.367E−04 | 0.369E−04 | 0.370E−04 |
| time(s) | $c = ([C_2H_6]_t + [C_4H_{10}]_t)/\Delta[CH_4]_t$ | | |
| 1.0E−02 | 0.197E+00 | 0.235E+00 | 0.338E+00 |
| 1.0E−01 | 0.111E+00 | 0.151E+00 | 0.202E+00 |
| 1.0E+00 | 0.153E+00 | 0.185E+00 | 0.190E+00 |
| 1.0E+01 | 0.335E+00 | 0.360E+00 | 0.368E+00 |
| 1.0E+02 | 0.266E+00 | 0.279E+00 | 0.283E+00 |
| 1.0E+03 | 0.257E+00 | 0.268e+00 | 0.272E+00 |

$\Delta[CH_4]_t = [CH_4]_{initial} - [CH_4]_t$
$\kappa = \Delta[CH_4]_t/[CH_4]_{ini}$ is the net fraction converted at time t
$\Delta = [CO]_t/\Delta[CH_4]_t$ is the fraction lost by oxidation
(a) = $[CO + H_2]_t/\Delta[CH_4]_t$ fraction converted to local heating fuel
(b) = $[C_2H_4 + C_3H_6]_t/\Delta CH_4]_t$ fraction converted to olefines
(c) = $[C_2H_6 + C_4H_{10}]_t/\Delta[CH_4]_t$ fraction converted to paraffins.

From Table I, optimal operational conditions may be selected for any acceptable level of conversion that is compatible with the cost of the initiator. Accordingly, the initiator may be a major constituent of gasoline, such as iso-octane, to keep the costs of the conversion process within commercial limits.

Figure 2A:
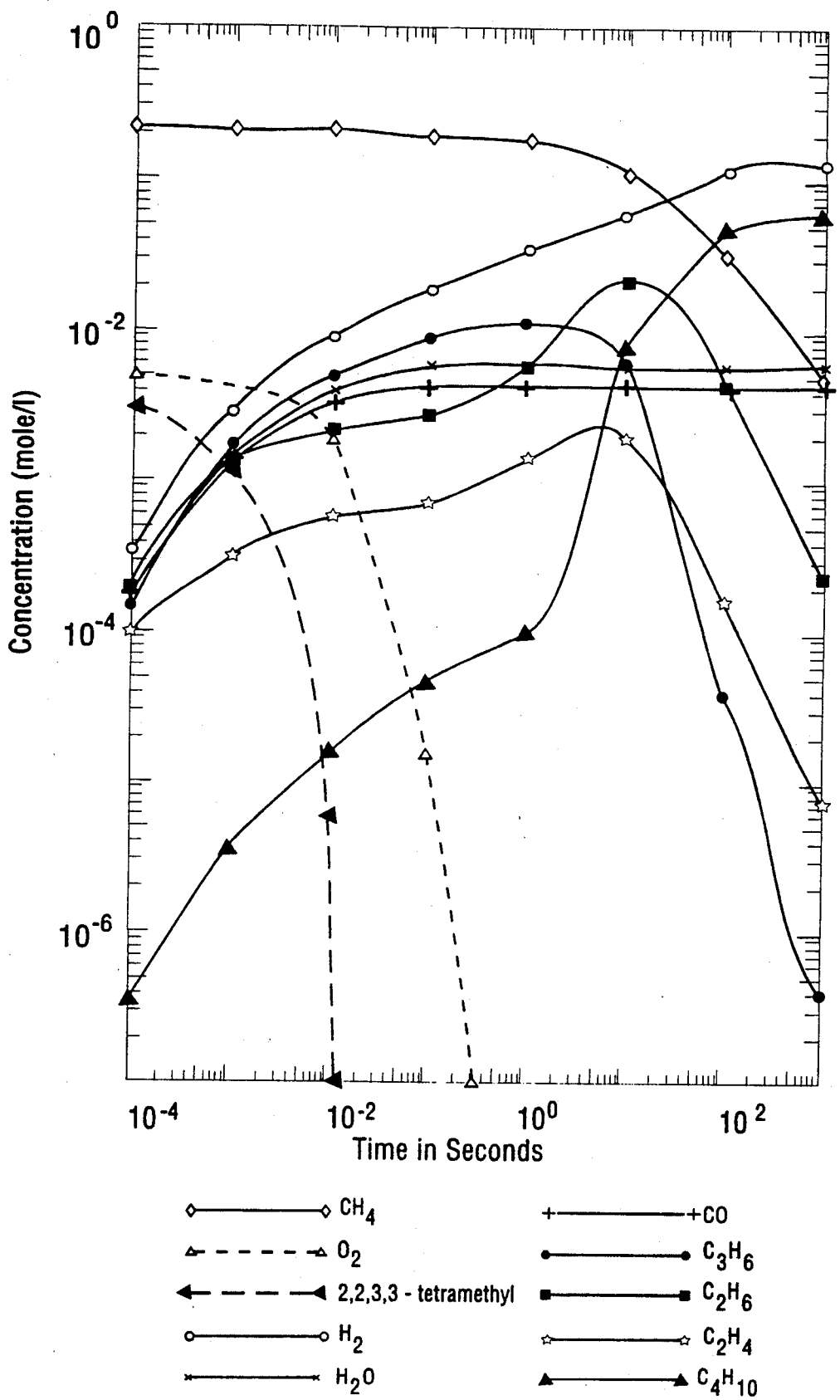
FIGS. 2a through 2c in graphical view the time-dependent product distributions of the methane conversion method of the invention, utilizing different initiators and different initiator concentrations.
Figure 2B:
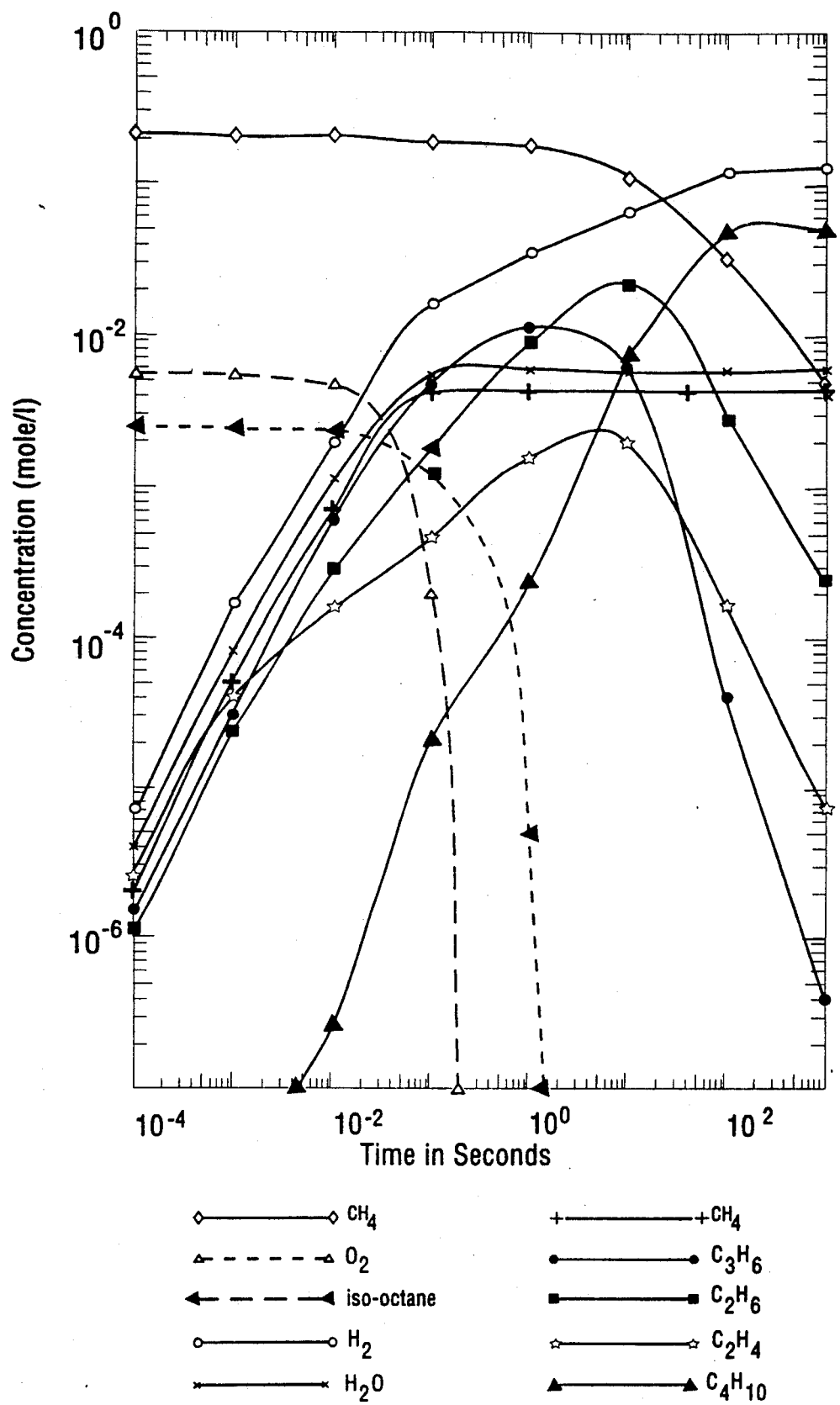
Figure 2C:
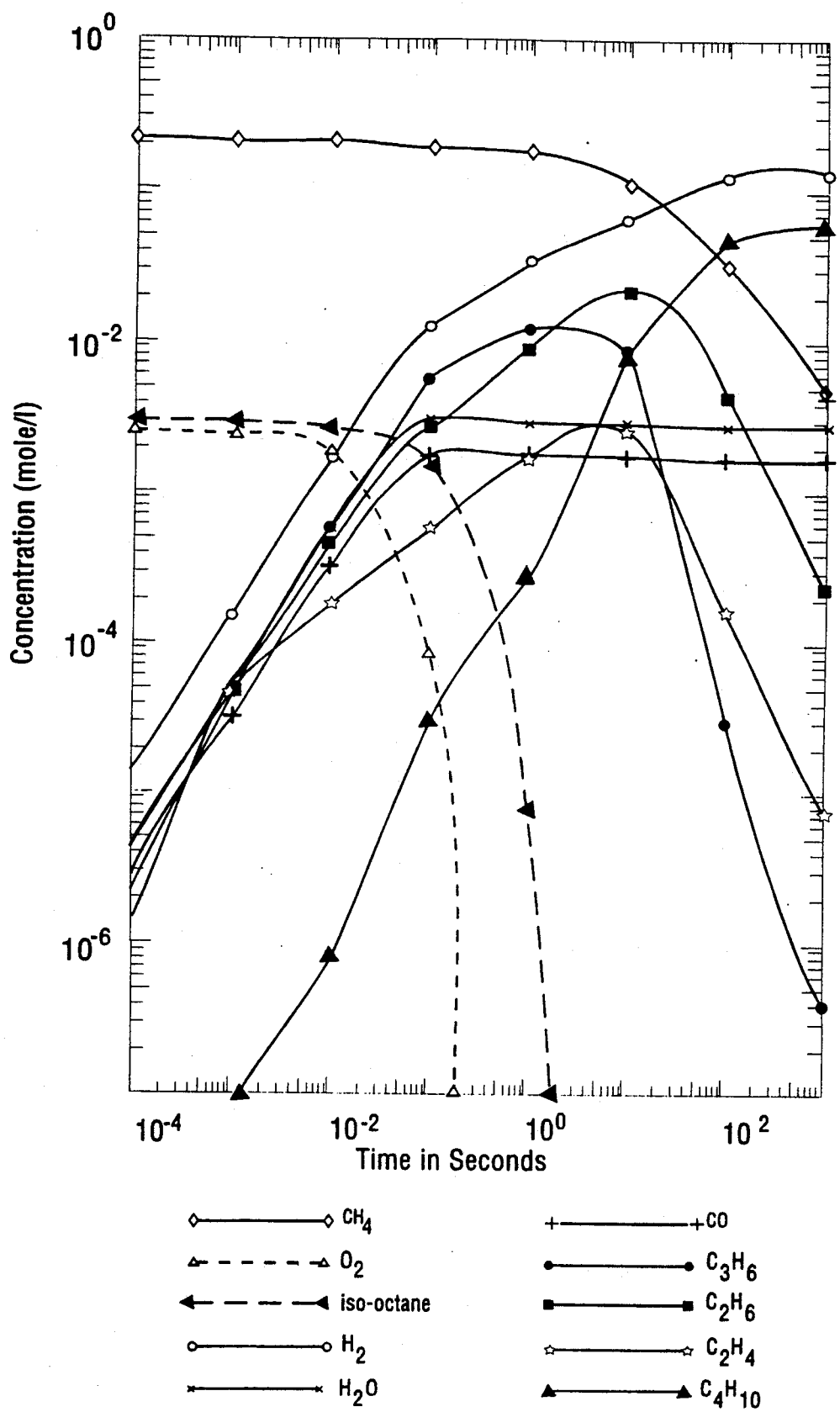

Referring to FIGS. 2a through 2c, the conversion process of methane is graphically represented with respect to temperature and pressure, utilizing (in FIG. 2a) 2,2,3,3-tetramethyl butane and (in FIGS. 2b and 2c) iso-octanes as initiators.

FIGS. 2a through 2c illustrate how, during the early stages of the conversion process, CH3 radicals play a critical role in generating ethane and propene. The conversion process is then carried forward by an extended mixture of radicals. In about 0.4 seconds, oxygen is essentially depleted; the initiator becomes depleted at an earlier time, at about 0.02 seconds. Butane levels grow rapidly between 1.0 and 10.0 seconds.

Some of the characteristics of useful initiators include the following: (a) the initiator dissociates homogeneously and rapidly into radicals and/or H atoms at temperatures below 1,000°-1100°K.; (b) the radicals react rapidly with molecular oxygen to generate additional radicals to develop a branched chain reaction; and (c) the radicals rapidly attack methane by abstracting hydrogen atoms.

The initiators need only one other characteristic in order to provide a commercial process: that is cost. Availability at modest cost is essential to achieve commercialization.

FIGS. 2a through 2c illustrate the successful performance of the conversion process, i.e., (a) substantial levels of methane can be converted by a thermal process to ethane, propene and butane without the presence of a catalyst; (b) conversion is accomplished by a free radical initiator at low concentrations of the initiator augmented by a correspondingly low concentration of oxygen; (c) the efficiency and selectivity of the conversion can be manipulated by control of the pressure, temperature and composition of the gaseous mixture; and (d) the conversion process is accomplished without runaway oxidation of the methane.

Referring to FIGS. 2a through 2c, the conversion process is graphically illustrated for two different types of initiators—2,2,3,3-tetramethyl butane and an iso-octane (2,2,4-trimethyl pentane). The latter initiator was chosen due to its availability at a low cost and its substantial volume.

It is calculated that nearly all highly methylated butanes and pentanes that incorporate at least one tertiary carbon atom would serve as useful initiators. The commercialization of the conversion process will depend upon balancing the product yield versus the cost and availability of the chosen initiator. Methylated alkanes fission (unimolecularly) at temperatures in the range of approximately 800° C. to 850° C. The fission creates two free radicals, each of which loses an H atom to become the more stable alkene. The H atoms initiate a branched chain attack on the molecular oxygen to product two radicals, both of which react with the methane. An extended sequence of C—H bond-breaking and C13 C bond-making subsequently takes place.

With respect to the east of the fission step, the preferred initiator would be a 4,4-dimethyl pentene-1, followed by a 2,2,3,3-tetramethyl butane. However, since neither of these is now available in sufficient quantity the iso-octane (2,2,4-trimethyl pentane) becomes a favored initiator for the methane conversion process. The iso-octane is a product of gasoline production and is available in sufficient quantities at low cost, able to serve as the initiator needed for commercialization. Iso-alkenes would serve well as initiators, but for their cost and availability.

For purposes of this invention, the chosen initiators are meant to be exemplary of the overall inventive process, whose selected and chosen yields must be balanced against the chosen initiator to provide the most cost-effective conversion. The added air, as a source of oxygen, is crucial.

Since other modifications and changes varied to fit particular operating requirements and environments will be apparent to those skilled in the art, the invention is not considered limited to the examples chosen for purposes of disclosure, and covers all changes and modifications which do not constitute departures from the true spirit and scope of this invention.

Having thus described the invention, what is desired to be protected by Letters Patent is presented by the subsequently appended claims.

What is claimed is:

1. A method of converting methane to higher molecular weight hydrocarbons in the absence of a catalyst, comprising the steps of:
  a) mixing methane with an alkylated hydrocarbon serving as free radical initiator, and oxygen, in the absence of a catalyst, both said free radical initiator and said oxygen being in maximum concentrations of approximately two percent with respect to said methane, to form a reactive mixture;
  b) heating said reactive mixture to a temperature of at least approximately 775° C. to cause production of free radicals, and subsequent production of higher molecular weight hydrocarbons; and
  c) separating and collecting said higher molecular weight hydrocarbons.

2. The method of claim 1, wherein said alkylated hydrocarbon comprises a hydrocarbon having at least one tertiary carbon.

3. The method of claim 2, wherein said alkylated hydrocarbon comprises a tetramethyl-substituted butane.

4. The method of claim 2, wherein said alkylated hydrocarbon comprises a trimethyl-substituted pentane.

5. The method of claim 3, wherein said alkylated hydrocarbon comprises 2,2,3,3-tetramethyl butane.

6. The method of claim 4, wherein said alkylated hydrocarbon comprises 2,2,4-trimethyl pentane.

7. The method of claim 2, wherein said alkylated hydrocarbon comprises a mixture of methylated alkanes.

8. The method of claim 2, wherein said alkylated hydrocarbon comprises an alkene.

9. A method of converting methane to higher molecular weight hydrocarbons in the absence of a catalyst, comprising the steps of:
  a) mixing methane with at least one multi-branched hydrocarbon free radical initiator and oxygen in the absence of a catalyst, both said multi-branched hydrocarbon free radical initiator and said oxygen being in maximum concentrations of approximately two percent with respect to said methane, to form a reactive mixture;
  b) heating said reactive mixture to a temperature sufficient to cause production of free radicals, and subsequent production of higher molecular weight hydrocarbons; and
  c) separating and collecting said higher molecular weight hydrocarbons.

10. The method of claim 9, wherein said multi-branched hydrocarbon free radical initiator comprises an alkyl-substituted hydrocarbon.

11. The method of claim 10, wherein said alkyl-substituted hydrocarbon is further characterized as a methylated hydrocarbon chain having at least one tertiary carbon.

12. The method of claim 10, wherein said alkyl-substituted hydrocarbon comprises a methylated butane.

13. The method of claim 10, wherein said alkyl-substituted hydrocarbon comprises a methyl-substituted pentane.

14. The method of claim 12, wherein said methylated butane comprises 2,2,3,3-tetramethyl butane.

15. The method of claim 13, wherein said methylated pentane comprises 2,2,4-trimethyl pentane.

16. The method of claim 10, wherein said alkyl-substituted hydrocarbon comprises a mixture of methylated alkanes.

17. The method of claim 10, wherein said alkyl-substituted hydrocarbon comprises methylated alkenes.

* * * * *

UNITED STATES PATENT AND TRADEMARK OFFICE
CERTIFICATE OF CORRECTION

PATENT NO. : 5,214,226
DATED : May 25, 1993
INVENTOR(S) : Simon H. Bauer et al

It is certified that error appears in the above-indentified patent and that said Letters Patent is hereby corrected as shown below:

Col. 1, line 19: between "methane" and "an", insert --as--.
Col. 1, line 44: delete dash at end of line and add --$H_2O$].-- thereto, effectively deleting line 45.
Col. 2, line 24: add --y-- to "difficult".
Col. 4, line 48: delete the second "preheated" in the line, and substitute therefor --preheater--.
Col. 7, line 26: delete "Cl3" and substitute therefor --C-C--.
"      line 28: delete "east" and substitute therefor --ease--.

Signed and Sealed this

Fifteenth Day of March, 1994

Attest:

BRUCE LEHMAN

Attesting Officer          Commissioner of Patents and Trademarks